(12) United States Patent
Taylor et al.

(10) Patent No.: US 7,807,865 B1
(45) Date of Patent: Oct. 5, 2010

(54) **TRANSGENE ASSAY USING STABLE *AGROBACTERIUM RHIZOGENES* TRANSFORMATION**

(75) Inventors: Christopher G Taylor, Ballwin, MO (US); Yong Huang, Madison, WI (US)

(73) Assignee: Monsanto Technology LLC, St. Louis, MO (US)

( * ) Notice: Subject to any disclaimer, the term of this patent is extended or adjusted under 35 U.S.C. 154(b) by 834 days.

(21) Appl. No.: 09/386,605

(22) Filed: Aug. 31, 1999

Related U.S. Application Data

(60) Provisional application No. 60/098,402, filed on Aug. 31, 1998.

(51) Int. Cl.
*C12N 15/83* (2006.01)
*C12N 15/11* (2006.01)
*C12N 15/00* (2006.01)

(52) U.S. Cl. .................... 800/278; 800/294; 435/230.1; 536/23.1

(58) Field of Classification Search .................... 435/6, 435/410, 419, 243, 252.3, 320.1; 536/23.1, 536/23.6, 23.7, 24.1, 23, 23.2; 800/278, 800/294, 295, 312, 317.2, 317.4
See application file for complete search history.

(56) References Cited

FOREIGN PATENT DOCUMENTS

| EP | 0 204 590 A | 12/1986 |
|---|---|---|
| EP | 0 262 972 A | 4/1988 |
| EP | 0 334 383 A | 9/1989 |

OTHER PUBLICATIONS

Burch. Annu. Rev. Plant Physiol. Plant Mol. Biol., 1997, 48:297-326.*
Rech, et al. Plant Cell Reports, 1989, 8:33-36.*
(Raven et al, Biology of Plants (1992), Worth Publishers, New York, NY 10003, pp. 382, Table 18, and 494-5, Figures 23-8, 23-9 and 23-10).*
Simpson et. al. (1986) Plant Mol. Biol. vol. 6, pp. 403-415.*
Savka et. al. (1990) Phytopathology vol. 80, pp. 503-508.*
Hatamoto et al. Recovery of morphologically normal tranasgenic tobacco from hairy roots co-transformed with Agrobacterium rhizogenes and a binary vector plasmid. *Plant Cell Reports*. 9(9):88-92 (1990).
Murashige et al. A revised medium for rapid growth and bio assays with tobacco tissue cultures. *Physiologia Plantarum*. 15:473-497 (1962).
Shahin et al. Transformation of cultivated tomato by a binary vector in Agrobacterium rhizogenes: transgenic plants with normal phenotypes harbor binary vector T-DNA, but no Ri-plasmid T-DNA. *Theoretical and Applied Genetics*. 72(6):720-777 (1986).
Simpson et al. A disarmed binary vector from Agrobacterium tumefaciens functions in Agrobacterium rhizogens. *Plant Molucular Biology*. 6(6):403-415 (1986).

* cited by examiner

*Primary Examiner*—Anne Marie Grunberg
*Assistant Examiner*—Brent Page
(74) *Attorney, Agent, or Firm*—Thomas P. McBride, Esq.; Sonnenschein Nath & Rosenthal LLP

(57) ABSTRACT

A novel method is described for the screening of gene elements of interest using hairy roots of chimeric plants transformed with *Agrobacterium rhizogenes*.

5 Claims, 3 Drawing Sheets

TRANSGENE ASSAY USING STABLE *AGROBACTERIUM RHIZOGENES* TRANSFORMATION

This application claims priority from U.S. provisional patent application No. 60/098,402, filed Aug. 31, 1998, herein incorporated by reference in its entirety.

FIELD OF THE INVENTION

The present invention relates in general to a new method of screening genetic elements of interest for functionality, and more particularly to such a method utilizing *Agrobacterium rhizogenes* to transform plant tissue in a manner forming a chimeric plant expressing or containing the genetic element of interest in transgenic root tissue.

BACKGROUND OF THE INVENTION

*Agrobacterium rhizogenes* is a soil bacteria that is known to infect wounded root tissue and that transfers a portion of its bacterial plasmid, the Ri plasmid, to the plant. The Ri-T-DNA that is transferred to the plant induces the formation of adventitious roots and these genetically transformed roots can be regenerated into whole plants that transmit the Ri T-DNA to their progeny. *Agrobacterium rhizogenes* has, therefore, been used to generate stably transformed whole plants. In one application of this technology, secondary metabolites can be produced from culture using this method.

With the advent of genomics-based discovery of genes and genetic elements, new methods are needed to facilitate the rapid screening of the large numbers of genes (or genetic elements) that are becoming available. Typically, genes of interest are cloned and then stably transformed using *Agrobacterium tumefaciens* mediated delivery or by a particle gun method into plants for functional analysis of the gene or genetic element. This method can take up to 9 months for transgenic plants, such as soybean, to be transformed and ready for testing. This is a slow and inefficient process. Therefore, there is a need for a rapid method of screening large numbers of genes and gene constructs in planta for functionality.

SUMMARY OF THE INVENTION

The present invention relates to a rapid, in planta method for screening a genetic element for functional activity. It has been discovered that by utilizing *Agrobacterium rhizogenes* to transform plant tissue in a manner producing a chimeric plant having only transgenic root tissue, with the remainder of the plant being non-transgenic, transgenic tissue containing a selected genetic element can be available for testing without having to produce stably transformed whole plants. The method greatly reduces the time required to screen large numbers of genetic elements and permits functional testing in about 2 to 3 months from the start of the transformation process.

Therefore, in one preferred embodiment, the present invention provides a method for producing a stable chimeric plant having transgenic root tissue that comprises obtaining an explant, inoculating the explant with *Agrobacterium rhizogenes* containing an exogenous genetic element capable of being transferred to the explant, culturing the inoculated explant in a manner permitting transgenic root development, and producing a stable chimeric plant with transgenic root tissue. This transgenic root tissue is available for testing of the functionality of the genetic element introduced therein by standard methodology relevant to the genetic element being tested.

Among the many aims and objectives of the present invention include the provision of a method providing for an in planta assay for testing genes for anti-pathogen or anti-insect activity; testing genes for enzymatic or metabolic activity; high-throughput gene trapping, promoter trapping, and enhancer trapping; optimizing constructs for gene expression and protein production; testing constructs for gene expression before submission for production of transgenic plants; and production of large amounts of protein. Moreover, the present method provides a method of producing chimeric plants in soil, not in tissue culture, thereby greatly reducing the possibility of contamination and avoiding the disadvantages associated with regenerating transgenic plants through tissue culture methods.

Also provided are chimeric soybean plants produced by the method described herein.

DETAILED DESCRIPTION OF THE INVENTION

Figure 1:
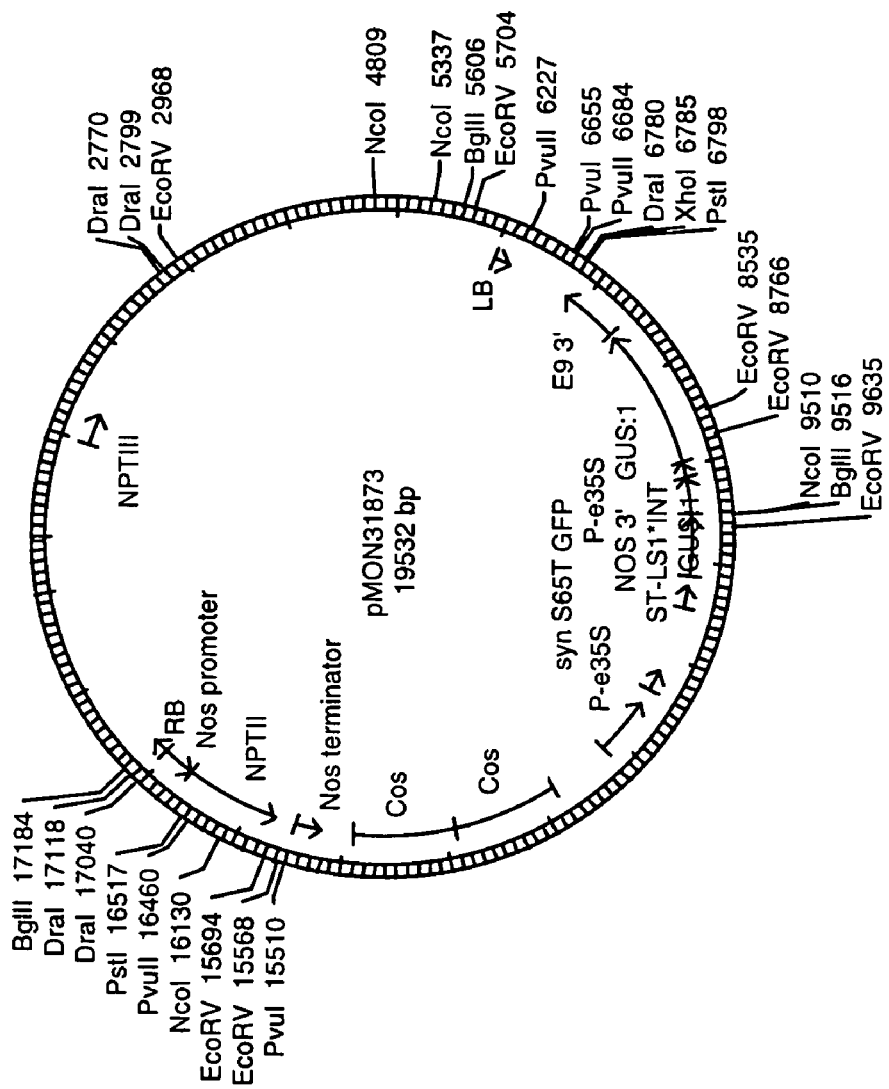
FIG. 1 is a representation of the plasmid map for pMON31873.

In order to provide a clear and consistent understanding of the specification and the claims, including the scope given to such terms, the following definitions are provided.

A "chimeric plant" is a plant with only a portion of its cells transgenic. In the following examples the chimeric plants are defined as having transgenic roots but wild-type shoots, stems, and leaves.

A "genetic element of interest" can be a promoter, an intron, a structural gene, a fragment of a gene, a 3' terminator, an enhancer, or any other genetic element that might affect gene expression, gene functionality, or a combination thereof.

"Expression" means the combination of intracellular processes, including transcription and translation, undergone by a coding DNA molecule such as a structural gene to produce a polypeptide.

"Promoter" means a recognition site on a DNA sequence or group of DNA sequences that provides an expression control element for a structural gene and to which RNA polymerase specifically bind and initiates RNA synthesis (transcription) of that gene.

"Regeneration" means the process of growing a plant from a plant cell (e.g., plant protoplast or explant).

"Structural gene" means a gene that is expressed to produce a polypeptide.

"Structural coding sequence" refers to a DNA sequence that encodes a peptide, polypeptide, or protein that is made by a cell following transcription of the structural coding sequence to messenger RNA (mRNA), followed by translation of the mRNA to the desired peptide, polypeptide, or protein product.

"Transformation" refers to a process of introducing an exogenous DNA sequence (e.g., a vector, a recombinant DNA molecule) into a cell or protoplast in which that exogenous DNA is incorporated into a chromosome or is capable of autonomous replication.

"Vector" means a DNA molecule capable of replication in a host cell or to which another DNA segment can be operatively linked so as to bring about replication of the attached segment. A plasmid is an exemplary vector.

"Exogenous" as used herein means any genetic element that is not naturally occurring in a wild-type *Agrobacterium rhizogenes* organism According to the present invention, there is provided a method for the rapid in planta testing of an exogenous genetic element in a chimeric plant. The plant is produced by transformation with *Agrobacterium rhizogenes*. This process requires the use of a wild-type *Agrobacterium rhizogenes* strain that transfers genes that encode for production of plant growth regulators that stimulate hairy root formation to the infected plant tissue during the transformation process. Numerous strains of *Agrobacterium rhizogenes* are known, and any strain that efficiently transforms the plant of interest may be used. It is understood, however, that some strains are more virulent than others and certain strains may not be used with all plant species because of the level of virulence. Thus, the plant species being transformed and the strain of *Agrobacterium rhizogenes* being used should be compatible. Most preferably, the highly virulent strain K599 is used with plant species such as soybean and potato, but a less virulent strain may be needed for tomato.

In addition to the wild-type *Agrobacterium rhizogenes* strain that is to be used for the transformation, a construct containing the genetic element to be tested for functionality in planta is added to the *Agrobacterium rhizogenes* in the form of a binary plasmid, a piece of circular DNA. The plasmid may take many forms known in the art, but typically requires an origin of replication that allows for stable plasmid retention in *Agrobacterium rhizogenes*; a suitable selectable marker resistance gene that allows for selection of the plasmid in *Agrobacterium rhizogenes*; two DNA border sequences that determine the beginning and end points of the DNA that is to be transferred to the plant cell; and a construct containing the genetic element to be tested that is flanked by the before mentioned DNA border sequence. The construct containing the genetic element of interest will typically include in linear sequence a promoter, promoter elements, a structural gene, and a 3' terminator, and the genetic element being tested may be any one of these elements.

Suitable selectable marker genes include, but are not limited to, antibiotic resistance markers such as the neomycin phosphotransferase gene, which confers resistance to kanamycin. Other preferred selectable markers are genes that confer tolerance to the glyphosate herbicide as described in U.S. Pat. Nos. 5,463,175 and 5,633,435, herein incorporated by reference.

If the genetic element being tested is a promoter sequence, the construct will require a reporter gene. Suitable reporter genes include, but are not limited to genes encoding for green fluorescent protein (GFP), β-glucuronidase (GUS), chloramphenicol acetyl transferase (CAT), and luciferase.

If the gene element of interest is a structural gene, the construct will require the elements needed for expression of the structural gene in a plant, including a promoter sequence and a 3' non-translated termination/polyadenylation site and, optionally, an intron. Suitable promoters include constitutive or root-specific promoters, such as, but not limited to, enhanced 35S promoter from cauliflower mosaic virus (e35S CaMV), figwort mosaic virus promoter (FMV), the sugarcane badnavirus promoter, the actin promoter from rice, the ubiquitin promoter from maize, the nos promoter, the RB7 promoter, and the 4AS1 promoter. Any suitable 3' non-translated regions may be included in the vector containing the genetic element to be tested, including but not limited to the 3' region from the Agrobacterium tumor inducing (Ti) plasmid gene, such as the nopaline synthase gene (nos), and plant genes such as the soybean 7s storage protein gene and pea ssRUBISCO E9 gene. Suitable introns are known in the art and may include the intron from the rice actin gene or an intron from a wheat heat shock protein.

Methods for constructing the vectors as described herein and means for introducing such vectors into *Agrobacterium rhizogenes* are described in the relevant literature, such as Sambrook et al. (*Molecular Cloning: A Laboratory Manual*, Second Edition, Cold Spring Harbor Laboratory Press, Cold Spring Harbor, N.Y., 1989) or Ausubel et al. (*Current Protocols in Molecular Biology*, John Wiley and Sons, New York, N.Y., 1995).

A structural gene being tested in the method of this invention may be any structural gene that might confer a beneficial trait to a plant, including but not limited to agronomic traits such as herbicide tolerance, yield improvements, insect or pathogen resistance, or quality traits such as enhanced or improved nutritional value, or other proteins, enzymes or other biological product that may be produced in a plant.

Once the vector containing the genetic element to be tested is introduced into the *Agrobacterium rhizogenes*, a suitable explant from the plant to be transformed is selected. The explant is derived from the plant of choice such that after inoculation with the vector containing *Agrobacterium rhizogenes*, the explant is capable of generating transgenic roots and maintaining a normal, non-transgenic stem, leaves and other plant structures. Preferably, the explant is a stem, hypocotyl or other like structure. Most preferably, the explant is a hypocotyl obtained by removing the roots from a growing cotyledon by cutting the hypocotyl about 2-3 cm below the cotyledonary leaves. It is also preferable to remove the plant tissue above the cotyledonary leaves as well.

The explant is inoculated by contacting a cut or wounded portion of the explant with a solution containing the *Agrobacterium rhizogenes* for a period of time suitable to permit transfer of the DNA to the explant. This typically occurs when the filter is dry. When the filter is air dried, it can take up to a week, but other methods of drying may also be used that would take less time. The *Agrobacterium rhizogenes* may be contacted by dipping the cut explant into the solution or vacuum infiltration methods may be used. The bacterial solution may also be injected into the explant by methods known in the art.

Chimeric plants are produced from transgenic roots after transformation with *Agrobacterium rhizogenes*. Root growth can be initiated by placing the inoculated end of the plant into liquid or solid media containing minimal salts media (i.e., ¼ strength Murashige and Skoog Salt Mixture (MS) [Gibco-BRL, Cat. No 11117-074]). Hairy root formation can be observed between two and three weeks after transformation with *Agrobacterium rhizogenes*. Once roots begin to grow, the entire plant may be planted in soil or grown hydroponically. Generally, between 40 and 90% of the hairy roots generated will be transformed with the gene element of interest. All transgenic root growth is supported by the resources produced in the wild type shoots, stems, and leaves. This method relies on the cotyledons or excised shoots to provide the necessary resources for hairy root production, thus eliminating the need for sugars or other carbon sources that would allow for easy contamination of the media. Production of hairy roots can be done in a non-sterile field or lab bench thus eliminating the need for sterile hoods and sterile lab equipment.

Once the transgenic roots are established, the genetic element introduced into the plant may be analyzed using any of the methods familiar to those of skill in the art and appropriate for determining the functionality of the genetic element, including, but not limited to, immunochemical blots, Northern blots, Southern blots, extractions, plant pathogen assays, nodulation assays, enzyme assays, targeting assays, gene silencing assays, recombination assays, gene excision, functional genomics assay, PCR, and the like.

EXAMPLES

The following examples further illustrate the present invention. They are in no way to be construed as a limitation in scope and meaning of the claims.

Example 1

Transformation of Soybeans

Seed Sterilization

Petri dishes are filled with soybean seed and placed in a vacuum desiccator. A beaker containing 200 mL of bleach and 2 mL of concentrated HC1 is placed in the middle of a desiccator covered and vacuum applied. The vacuum is closed, and the seeds are allowed to sit for 16 to 24 hrs.

Germinate Seeds

Pots are filled with silica sand and the sterilized soybean seed is planted. The seed is germinated in a greenhouse for 7 days or until first leaf expands. It is preferable that the soybean seeds are grown in the greenhouse as this seems to improve the stability of the growing hypocotyl. First leaves are removed by cutting stem above cotyledons. The seedlings are transferred to a cold room at 4-6° C. (can be stored for up to seven days).

Inoculation

*Agrobacterium rhizogenes* strain K599 containing the genetic element to be tested is grown in LB media plus a plasmid selectable antibiotic in a 30° C. shaker overnight. The cells are spun down by centrifugation (4,000×g, 10 min.) and resuspended in Agro resuspension solution (1/10 strength B5 media plus 200 µM acetosyringone, 1 mM galacturonic acid, and 20 mM MES (pH5.4) to final $OD_{600\ nm}$=0.3). SORBAROD filters (Ilacon Limited, type 7006, or Sigma, S6404, St. Louis, Mo.) that have been placed into a petri plate or microtiter plate are saturated with Agro resuspension solution. Remaining area of well or plate is filled with Agro resuspension solution (minus the Agro). Soybean hypocotyls are cut about 2-3 cm below cotyledons and cut end of hypocotyls is placed into filters and vacuum infiltrated for 5 minutes. The hypocotyls are placed in a growth chamber at 22° C., 18 hr. light/6 hr. dark photo-period and the filters are permitted to dry until all of the Agro resuspension solution has evaporated and the filters have completely dried.

Root Initiation

There are two options (chambers or plates) for root initiation.

Chambers (1)

Find empty pipette tip boxes and remove lids. Sterilize in autoclave. Cover top with thin sheet of aluminum foil. Punch number of holes as needed. Fill chamber with ¼ strength MS solution (pH 5.4) (optional is the addition of low levels of selectable agents, i.e., kanamycin 50 mg/L). Hypocotyls are removed from filters and placed in holes. Keep chambers in Percival at 22° C., 18 hr. light 6 hr. dark photo-period.

Plates (2)

Prepare ¼ strength MS (pH 5.4) plus 0.7% phytagel solution. Autoclave. Cool and pour into wide petri plates (optional is the addition of low levels of selectable agents, i.e., kanamycin 50 mg/L). Remove hypocotyls from filters and place in phytagel. Keep plates in growth chamber at 22° C., 18 hr. light/6 hr. dark photo-period.

Soybean Plantlet Culture

Remove any adventitious roots that may appear (these are roots above cut site) until week three. If a large number of cotyledons appear to turn yellow, spray with fungicide by misting over top. Monitor water level and replace as needed with ¼ strength MS (pH 5.4). This can be added to the plates also. Do not let inoculated ends dry out. After three weeks roots should begin to grow from inoculated ends.

Hairy Roots

The number of transgenic hairy roots that form will be dependent on the cultivar. PI accessions tend to produce more hairy roots than cultivated varieties. On average between 5 and 10 independent transgenic roots can be produced per hypocotyl. Generally, between 40 and 70% of the hairy roots generated will be transformed with the genetic element introduced. In initiating roots in presence of low levels of selectable agents (kanamycin 50 mg/L) up to 90% of generated hairy roots will be transformed with the introduced genetic element. When transgenes are linked to reporter genes (i.e., GFP), transgenic roots can be selected based on expression of reporter genes.

Production of Chimeric Soybean Plants

Large amounts of hairy roots can be produced by planting the chimeric plants in soil or grown hydroponically. The plant provides most of the energy needed for hairy root growth. Only minimal salts are needed. Hairy root plants tend to be dwarf with early induced seed production.

Figure 2:
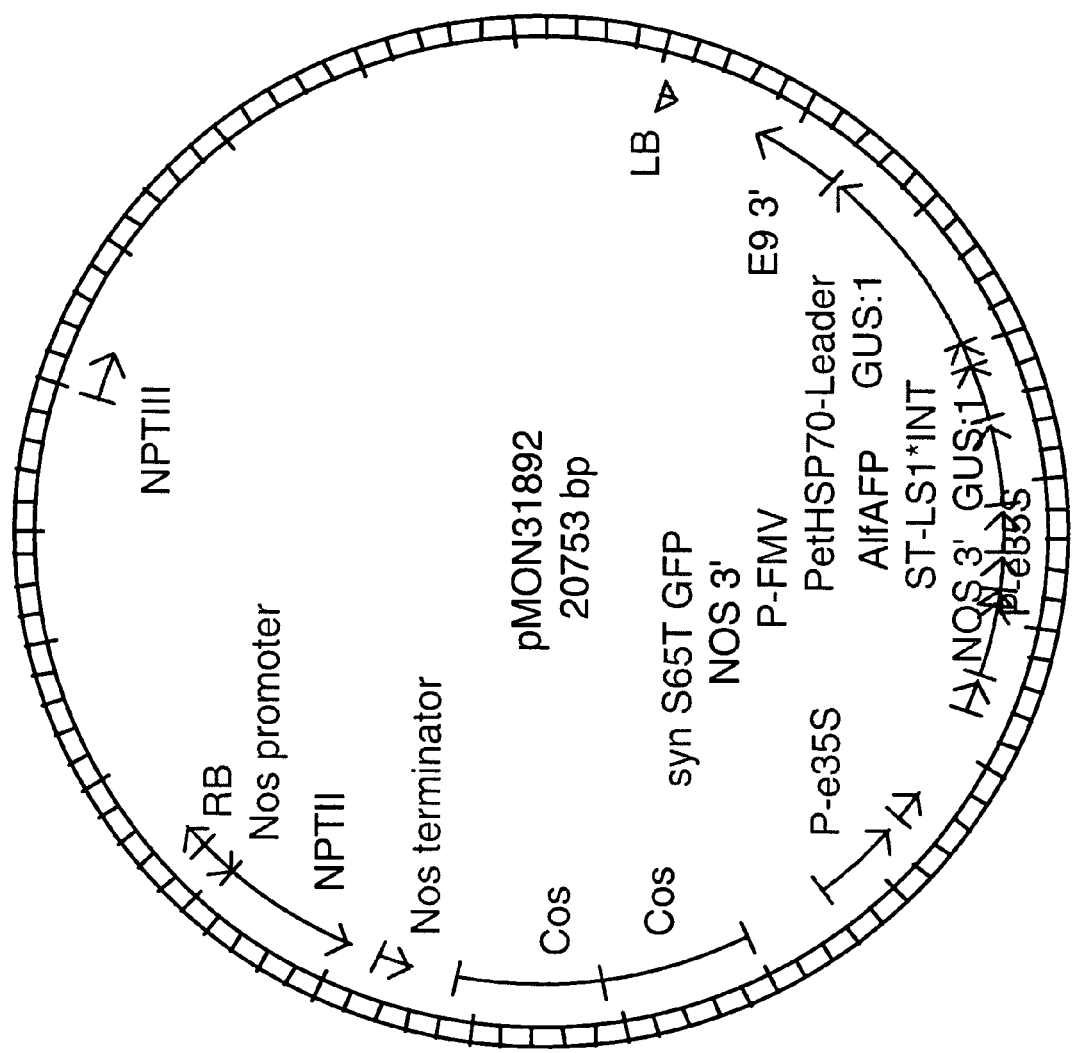
FIG. 2 is a representation of the plasmid map for pMON31892.
Figure 3:
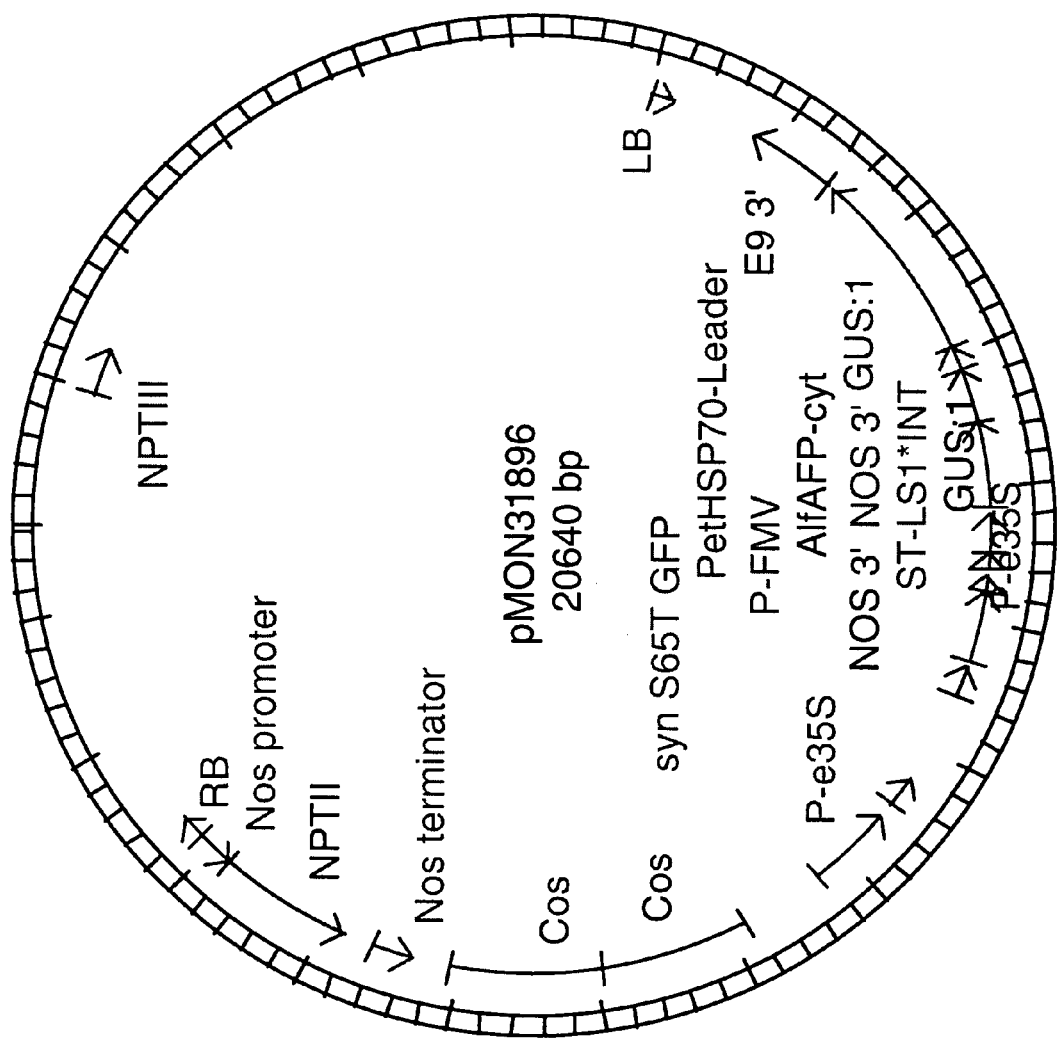
FIG. 3 is a representation of the plasmid map for pMON31896.

The example below represents a study done on expression of an anti-fungal protein (AFP) from alfalfa (Alf). Two binary plasmids were constructed from pMON31873 (FIG. 1) using the Figwort Mosaic Virus (FMV) constitutive promoter, to drive expression of a cytoplasmically (pMON31892; FIG. 2) or extracellularly (pMON31896; FIG. 3) targeted Alf-AFP. Each construct was additionally linked to an enhanced 35S promoter driving expression of the green fluorescence protein (GFP) and was used to produce transgenic hairy-roots as described above. Five weeks after transformation, transgenic roots were individually harvested, analyzed for GFP expression by observing green fluorescence under a UV light and frozen. Protein was extracted from root-tissues and used in a standardized ELISA assay using an antibody made specifically against Alf-AFP to determine the amount of Alf-AFP present. Table 1 shows results of the study.

TABLE 1

Expression of Alf-AFP and GFP in hairy roots of soybeans.

| Sample | PPM Alf-AFP | GFP yes/n |
|---|---|---|
| Vector Control | | |
| 1 | 0.009 | yes |
| Extracellular Alf-AFP | | |
| 1 | 0.069 | yes |
| 2 | 0.154 | yes |
| 3 | 0.021 | yes |
| 4 | 0.003 | no |
| 5 | 0.001 | no |
| 6 | 0.019 | no |
| Cytoplasmic Alf-AFP | | |
| 1 | 0.01 | no |
| 2 | 0.009 | no |
| 3 | 0.01 | no |
| 4 | 0.01 | no |
| 5 | 0.01 | yes |
| 6 | 0.01 | yes |
| 7 | 0.011 | no |
| 8 | 0.011 | yes |
| 9 | 0.011 | yes |
| 10 | 0.012 | yes |
| 11 | 0.01 | no |

The results from this experiment indicated that the extracellulary targeted Alf-AFP binary construct was capable of producing Alf-AFP in transgenic roots. A strong correlation between GFP positive roots and those that expressed Alf-AFP was observed. However, the cytoplasmically targeted version of Alf-AFP did not accumulate Alf-AFP. Because this construct was never tested, the expected result was uncertain. This example demonstrates how rapidly constructs can be screened for gene expression. Thus, one can quickly and cheaply screen for a genetic element of interest using this method of generating transgenic hairy roots.

Example 2

Transformation of Potato

For generation of hairy roots on potato the same solutions are used as described in Example 1. For plant material, potatoes that contain numerous branches are preferred. Potatoes do not need to be chilled prior to inoculation. Cut potato branches at nodes and place in Agro resuspension solution (1/10 strength B5 media plus 200 µM acetosyringone, 1 mM galacturonic acid, and 20 mM MES (pH5.4) to final $OD_{600\ nm}$=0.3). Vacuum infiltrate and place in growth chamber at 22° C., 18 hr. light/6 hr. dark photo-period.

Production of Chimeric Potato Plants

Potatoes produce hairy roots much more rapidly than soybean. Roots will begin to appear within two weeks. Adventitious roots generally do not appear. If they do, simply remove them with a scalpel. Co-transformation of hairy roots with a genetic element is between 70 and 90%. Up to 25 independent hairy roots may form per stem.

The example below represents a study done on expression of an anti-fungal protein (AFP) from alfalfa (Alf). Two binary plasmids were constructed from pMON31873 (FIG. 1) using the Figwort Mosaic Virus (FMV) constitutive promoter, to drive expression of a cytoplasmically (pMON31892; FIG. 2) or extracellularly (pMON31896; FIG. 3) targeted Alf-AFP. Each construct was additionally linked to an enhanced 35S promoter driving expression of the green fluorescence protein (GFP) and was used to produce transgenic hairy-roots. Five weeks after transformation, transgenic roots were individually harvested, analyzed for GFP expression by observing green fluorescence under a UV light and frozen. Protein was extracted from root-tissues and used in a standardized ELISA assay using an antibody made specifically against Alf-AFP to determine the amount of Alf-AFP present. Table 2 shows results of the study.

TABLE 2

Expression of Alf-AFP and GFP in hairy roots of potato.

| Sample | PPM Alf-AFP | GFP yes/no |
|---|---|---|
| Vector Control | | |
| 1 | 0.024 | yes |
| 2 | 0.017 | yes |
| Extracellular Alf-AFP | | |
| 1 | 0.226 | yes |
| 2 | 0.02 | no |
| 3 | 0.023 | yes |
| 4 | 0.074 | yes |
| 5 | 0.024 | yes |
| 6 | 0.057 | yes |
| 7 | 0.016 | no |
| 8 | 0.044 | yes |
| Cytoplasmic Alf-AFP | | |
| 1 | 0.022 | yes |
| 2 | 0.019 | yes |
| 3 | 0.017 | no |
| 4 | 0.015 | yes |
| 5 | 0.012 | yes |
| 6 | 0.011 | yes |
| 7 | 0.007 | yes |
| 8 | 0.004 | yes |

The results from this experiment indicated that the extracellulary targeted Alf-AFP binary construct was capable of producing Alf-AFP in transgenic roots. A strong correlation between GFP positive roots and those that expressed Alf-AFP was observed. However, the cytoplasmically targeted version of Alf-AFP did not accumulate Alf-AFP. Because this construct was never tested, the expected result was uncertain. This example demonstrates how rapidly constructs can be screened for gene expression. Thus, one can quickly and cheaply screen for a genetic element using this method of generating transgenic hairy roots.

All publications and patent applications mentioned in this specification are indicative of the level of skill of those skilled in the art to which this invention pertains. All publications and patent applications are herein incorporated by reference to the same extent as if each individual publication or patent application was specifically and individually indicated to be incorporated by reference.

Although the invention has been described in detail for the purpose of illustration, it is understood that such detail is solely for that purpose, and variations can be made therein by those skilled in the art without departing from the spirit and scope of the invention which is defined by the following claims.

What is claimed is:

1. A method for producing a stably transformed chimeric dicotyledonous plant having transgenic root tissue, the method comprising the steps of:

obtaining a stem or hypocotyl explant from a selected dicotyledonous plant species, wherein the hypocotyl explant has a cut end below the cotyledon;

transforming the stem or hypocotyl explant with *Agrobacterium rhizogenes* containing an exogenous nucleic acid sequence capable of being transferred to the explant, wherein the cut end of the hypocotyl explant is contacted with the *Agrobacterium rhizogenes*;

culturing the transformed explant in a root initiating media to produce transformed roots; and transferring the transformed roots to soil or a hydroponic environment to produce a chimeric dicotyledonous plant having transformed roots and wild type shoots, stems and leaves, wherein the dicotyledonous plant is soybean.

2. The method of claim 1 wherein transformed roots are initiated in the hypocotyl by placing the end of the hypocotyl contacted with the *Agrobacterium rhizogenes* in a media containing ¼ strength Murashige and Skoog media.

3. The method of claim 2 wherein the media further comprises a selectable agent.

4. The method of claim 3 wherein the selectable agent is kanamycin.

5. The method of claim 4 wherein the concentration of kanamycin in the media is no more than 50 mg/L.

* * * * *